United States Patent
Naqwi et al.

(10) Patent No.: US 7,072,051 B1
(45) Date of Patent: Jul. 4, 2006

(54) LASER DIFFRACTION PROCESS AND APPARATUS FOR WIDTH MEASUREMENT OF ELONGATED OBJECTS

(75) Inventors: Amir A. Naqwi, Shoreview, MN (US); Christopher W. Fandrey, Shoreview, MN (US)

(73) Assignee: Powerscope Incorporated, Minneapolis, MN (US)

(*) Notice: Subject to any disclaimer, the term of this patent is extended or adjusted under 35 U.S.C. 154(b) by 311 days.

(21) Appl. No.: 10/413,675

(22) Filed: Apr. 15, 2003

Related U.S. Application Data (60) Provisional application No. 60/379,820, filed on May 9, 2002.

(51) Int. Cl.
- G01B 11/02 (2006.01)
- G01N 21/86 (2006.01)
- G01V 8/00 (2006.01)

(52) U.S. Cl. .................. 356/635; 250/559.24
(58) Field of Classification Search ............. 356/635; 250/559.24; 700/157, 170
See application file for complete search history.

(56) References Cited

U.S. PATENT DOCUMENTS

| | | | |
|---|---|---|---|
| 3,812,376 A | 5/1974 | Takeyama et al. | 250/572 |
| 3,953,128 A | 4/1976 | Holly | 356/106 R |
| 3,982,816 A * | 9/1976 | Watkins | 356/73.1 |
| 4,009,965 A | 3/1977 | Pryor | 356/109 |
| 4,046,536 A * | 9/1977 | Smithgall, Sr. | 65/378 |
| 4,067,651 A * | 1/1978 | Watkins | 356/73.1 |
| 4,280,827 A | 7/1981 | Murphy et al. | 65/11 W |
| 4,343,637 A | 8/1982 | Shofner et al. | 65/2 |
| 4,363,827 A * | 12/1982 | Eichenbaum | 356/73.1 |
| 4,390,897 A | 6/1983 | Smithgall, Sr. | 358/101 |
| 4,847,509 A * | 7/1989 | Millet et al. | 356/73.1 |
| 4,854,707 A | 8/1989 | Ring et al. | 356/356 |
| 4,880,991 A | 11/1989 | Boehnlein et al. | 250/560 |
| 4,882,497 A | 11/1989 | Inoue et al. | 250/560 |
| 4,887,155 A | 12/1989 | Massen | 358/107 |
| 5,015,867 A | 5/1991 | Siegel et al. | 250/560 |
| 5,264,909 A | 11/1993 | Rochester | 356/73.1 |
| 5,309,221 A * | 5/1994 | Fischer et al. | 356/496 |
| 5,355,209 A | 10/1994 | Grosso | 356/73.1 |
| 5,432,605 A | 7/1995 | Naqwi et al. | 356/357 |
| 5,453,837 A | 9/1995 | Naqwi et al. | 356/357 |
| 5,513,004 A | 4/1996 | Naqwi et al. | 356/357 |
| 6,459,494 B1 | 10/2002 | Kurokawa et al. | 356/637 |
| 2002/0044289 A1 | 4/2002 | Blohm et al. | 356/635 |

OTHER PUBLICATIONS

"Fibre Sizing Using Fraunhofer Diffraction" by S.R. Powers et al., in *Optics Communications*, pp. 313–317, Sep. 1978.

* cited by examiner

*Primary Examiner*—Gregory J. Toatley, Jr.
*Assistant Examiner*—Gordon J. Stock, Jr.
(74) *Attorney, Agent, or Firm*—Westman, Champlin & Kelly (57) ABSTRACT

Size distribution of elongated objects is measured by forward scattering radiation from the objects at a range of scatter angles. The scattered radiation is refracted to locations on a scatter detector based on the scatter angles and independent of the location of the objects along the radiation axis. The intensity of radiation is sensed at each position on the scatter detector, and signals representative of the intensities at the positions are processed and compared to masks to identify a size distribution. The scatter detector may include individual radiation detectors arranged to receive refracted radiation representing respective ranges of scatter angles to thereby compensate for lower radiation intensities scattered from smaller objects.

24 Claims, 4 Drawing Sheets

LASER DIFFRACTION PROCESS AND APPARATUS FOR WIDTH MEASUREMENT OF ELONGATED OBJECTS

CROSS-REFERENCE TO RELATED APPLICATIONS

This application claims benefit of U.S. Provisional Application No. 60/379,820 filed May 9, 2002 for "Ensemble Laser Diffraction Method and Apparatus For Fiber Diameter Measurements" by Amir A. Naqwi.

STATEMENT REGARDING FEDERALLY SPONSORED RESEARCH OR DEVELOPMENT

This Invention was made with Government support under Contract No. DE-FC36-02GO12063 awarded by the Department of Energy. The government has certain rights in this invention.

FIELD OF THE INVENTION

This invention relates to measurement of elongated objects, and particularly to processes and apparatus for measuring widths of plural small elongated objects such as fibers and the like.

BACKGROUND OF THE INVENTION

Polymer and glass fibers are used in a variety of fibrous materials, including non-woven fabrics, composite materials, filter media and building insulation. Fiber diameter significantly affects the properties of the fibrous material, including material strength, pore size and thermal resistivity. For this reason, it is important to ascertain the size (width or diameter) of fibers for process control purposes while manufacturing the fibrous material and/or for cataloging or grading the manufactured fibrous material for intended purpose.

One well-known technique for fabrication of non-woven fibrous material is a meltblown technique. Material is heated (melted) in a furnace and extruded through a plurality of orfii. The molten material is further attenuated by an air stream that blows along the direction of extrusion. The material cools in the air stream to form elongated fibers. The fibers are collected on a rotating collection drum as a non-woven web of fibers. Fiber size is affected by the viscosity of the molten fiber material exiting the orfii and the air pressure and temperature that draws the material from the furnace and cools it. In some manufacturing environments, it is desirable to measure the fiber size as the fibers are formed in the air stream, before collection on the drum. The fiber size data could be used to control the manufacturing process to regulate air pressure and temperature and furnace temperature, thereby controlling the size of fibers forming the web. In other environments, samples of the completed web are collected from the drum and examined to measure the size of fiber in the web. The web from which the sample was taken is thereby cataloged or graded.

Existing techniques for measuring fiber size include direct microscopic measurement (including electron microscopy) and indirect measurement based on airflow resistance of a compacted fiber sample. These methods are time-consuming and do not provide a continuous signal suitable for process control. More particularly, during fabrication of a fibrous web, such as by the meltblown process, the fibers move in a continuous manner through the process steps. Real-time measurement of the width of the fiber during the process would be best accomplished by a non-contact technique.

Non-contact techniques for size measurement include digital imaging, back-scattered non-imaging techniques, laser interferometric techniques, and forward-scattered non-imaging techniques. Digital imaging measures the size of the elongated object. Conveniently, the digital imaging can be accomplished in a backward direction, so that the light source and the imaging device are located in the same measuring probe. An example of digital imaging technique to measure size may be found in U.S. Pat. No. 4,887,155. One problem of digital imaging is that it requires the object being measured be within the focal region of the imaging optics. Consequently, the process is not well suited for measuring objects that are freely flowing, such as in a meltblown process. Further, the imaging process is best suited for large objects (several hundred microns wide) and is not altogether suitable for fine objects (a few microns wide).

The back-scattered non-imaging technique uses back-scattered light intensity for size measurement. This technique is capable of measuring small object widths, but requires the objects be retained in a fixed plane. Consequently, this process is not well suited for measuring freely flowing objects. Moreover, the signal generated by this technique is affected by the optical properties of the objects, so the process is not well suited for measuring objects of varying optical characteristics. Where a plurality of elongated objects is being measured, the technique is capable of measuring only the mean size of the objects, and not a size distribution. See U.S. Pat. No. 4,343,637 to Shofner et al.

Interferometric laser techniques for non-contact real-time measurement of the size of elongated objects are described in U.S. Pat. No. 3,953,128 (Holly), U.S. Pat. No. 5,355,209 (Grosso et al.), U.S. Pat. No. 5,432,605 (Naqwi et al.), U.S. Pat. No. 5,453,837 (Naqwi) and U.S. Pat. No. 5,513,004 (Naqwi). These techniques work well for isolated cylindrical fibers of homogeneous material, but are not well suited for measuring fibers whose internal structures are not homogeneous. Consequently, the laser interferometric technique is not suitable for measuring fibers produced by several important fiber-generating processes, including meltblown processes, which produce fibers that are not homogeneous in internal structure. Moreover, the orientation of the objects must be substantially uniform, so the process is not well suited for identifying fiber sizes in non-woven web material that consists of long, narrow entangled fibers.

Forward-scattering non-imaging techniques employ forward scattering of light for size measurement of elongated objects. One forward-scattering technique, described in U.S. Pat. No. 3,812,376 (Takeyama et al.), U.S. Pat. No. 4,009,965 (Pryor), U.S. Pat. No. 4,854,707 (Ring et al.) and U.S. Pat. No. 4,880,991 (Boehnlein et al.), scans the object being measured with a laser beam. This method requires the object be mounted at a fixed position, and is best suited for measuring large-sized objects, such as machine parts. Another approach, described in U.S. Pat. No. 4,280,827 (Murphy et al.), U.S. Pat. No. 4,390,897 (Smithgall et al.), U.S. Pat. No. 4,882,497 (Inoue et al.) and U.S. Pat. No. 5,015,867 (Siegel et al.) fully illuminates the elongated object, but is useful only for measuring single objects. This technique can not measure plural elongated objects to obtain size distributions of objects present in the measurement region.

A variant of the forward-scattering technique, is described by Kurokawa et al. in U.S. Pat. No. 6,459,494, and measures the blockage of a laser beam by an elongated object. Thus, the Kurokawa device measures the shadow cast by the elongated object. Although a plurality of the objects is illuminated by a single light source, each object requires a dedicated detector and must be positioned at a fixed location from the detector in order to measure its size. Another variant is described by Rochester in U.S. Pat. No. 5,264,909, and employs a lens to image the shadow of the elongated object onto a detector array. Like the Kurokawa device, the Rochester device requires the object be precisely in focus for measurement. Thus, the Kurokawa et al. and Rochester devices cannot measure sizes of randomly-located and randomly-oriented objects.

Blohm et al., in published U.S. Patent Application No. US2002/0044289, describes a hybrid of the shadow and diffraction measurement techniques by placing the object at a controlled distance from the detector. This technique is useful only for measuring sizes of single objects and does not allow random location or random orientation of the object.

Powers and Somerford, in "Fiber Sizing using Fraunhofer Diffraction" published in Optics Communication, 1978, infer a width distribution of a plurality of elongated objects (fibers) using a forward scattering technique. The objects being measured are positioned in a fixed plane so that the scattering pattern is invariant at a fixed distance from the objects. This approach can not measure randomly-located fibers. Moreover, the Powers and Somerford approach is limited to measurement of opaque elongated objects or elongated apertures in an opaque screen. The detector proposed by Powers and Somerford cannot perform real-time measurement and cannot provide comparable sensitivity of the measurement to objects with small and large widths.

There is a need for a practical measurement device that measures sizes of a plurality of elongated objects at random orientations and/or locations.

SUMMARY OF THE INVENTION

The present invention is directed to a practical measurement technique utilizing a forward scatter configuration that allows measurement of a plurality of randomly-located and randomly-oriented elongated objects. The invention uses a radiation collection technique that enables real-time measurements with comparable sensitivity to objects of large and small widths.

In accordance with the present invention, size distribution of elongated objects is measured by scattering radiation from objects so that the scattering intensity as a function of scatter angles represents the size distribution of the elongated objects. The scattered radiation impinges a scatter detector at locations that are based on the scatter angles. The radiation intensity at each location on the scatter detector is sensed, and the size distribution of elongated objects is calculated.

In one embodiment of the invention, a radiation source emits a beam of collimated radiation along an axis. Radiation impinging elongated objects in a sensor region is scattered from its direction of propagation. Radiation scattered in the forward direction is detected by a forward scatter detector, which has a plurality of radiation detectors arranged at respective radial positions to the axis such that each detector is responsive to impinging radiation intensity to provide a signal representative of impinging radiation intensity. A lens is positioned to refract radiation scattered by the objects to radial locations on the scatter detector that are based on the forward scatter angles and without regard to the orientation or location of the objects in the sensor region.

In preferred embodiments, the radial widths of radially successive radiation detectors on the scatter detector increase exponentially from the axis. The radiation detectors are arranged by width so that the radiation detector having the largest width is most distal from the axis.

DETAILED DESCRIPTION OF THE PREFERRED EMBODIMENTS

The present invention is directed to measurement of elongated objects and is useful both for process control as well as fiber cataloging or grading. While the invention will be described in connection with measuring fibers, such as polymeric or glass fibers, the invention may be applied to measurement of other elongated objects, such as wire, and elongated objects formed of other material, such as metal. Moreover, the length of the object may be continuous, such as a continuous wire or thread, fixed length or indeterminate length. As used herein, "size" or "width" of elongated objects includes diameters and other dimensional measurements of an object smaller than its overall or perceived length, and not necessarily in a direction perpendicular to the length. Moreover, the size, or width, of an elongated object is not intended to define any particular shape of the object. Instead, the invention is applicable to measurement of various-shaped elongated objects, including cylindrical, conical, frusto-conical, rectilinear, prismatic, multifaceted, pyramidal and frusto-pyramidal objects. While the invention will be described in connection with optical techniques employing light radiation, particularly laser beams, the invention may be implemented using any convenient type of radiation, including radiation at a wavelength other than optical, such as infra-red (thermal) radiation, and other types of radiation, such as acoustic radiation.

Figure 1:
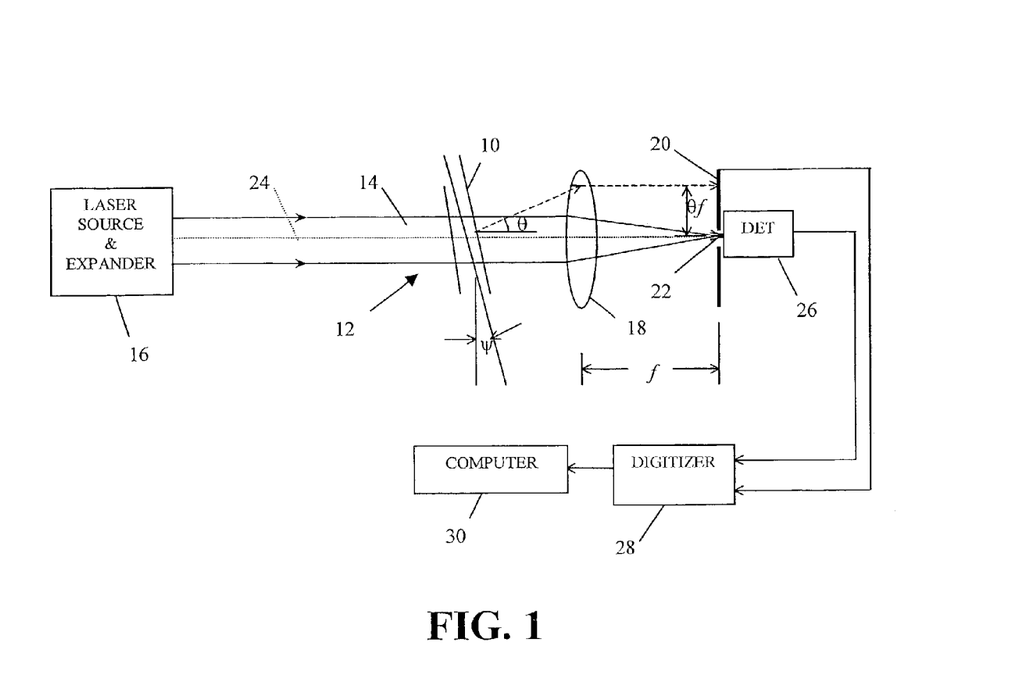
FIG. 1 is a schematic representation of apparatus according to a preferred embodiment of the present invention.

FIG. 1 is a schematic diagram of measurement apparatus in accordance with an embodiment of the present invention. A plurality of elongated objects 10, such as fibers, wires, a fibrous web, and the like, is positioned in a sensing region 12. A radiation beam 14, such as a collimated laser beam, is emitted from source 16. In preferred embodiments, source 16 comprises a laser source and an expander to collimate the radiation to form an expanded beam 14 with a diameter of about 1.0 cm. The radiation impinging objects 10 is forward scattered by the objects and is collected by a radiation receiving system 18, such as a lens, that transforms the scattered radiation onto radiation scatter detector 20. As used herein, "forward scatter" is the scattering of radiation in a generally forward (as opposed to backward) direction from the radiation source. Scattering of radiation is "forward" when angle θ shown in FIG. 1 is greater than 0° and not greater than 90°.

Figure 3:
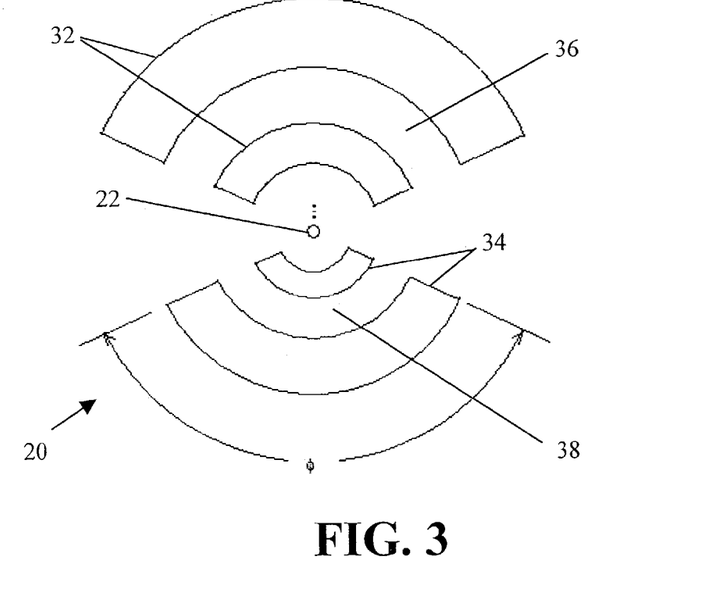
FIG. 3 is a plan view of a scatter detector used in the apparatus of FIG. 1.

In preferred embodiments, detector 20 is positioned 1.0 focal length f from lens 18 and consists of a plurality of radiation detectors 32, 34, shown in greater detail in FIG. 3. Scatter detector 20 is centered on beam 14 and includes a pinhole aperture 22 centered on central axis 24 of beam 14. Attenuation detector 26 receives light passing through aperture 22.

Scatter detector 20 and attenuation detector 26 provide analog signals representative of radiation intensity impinging the respective detector. The intensity signals from detectors 20 and 26 are supplied to digitizer 28, which converts the signals to digital signals representative of the respective radiation intensities, and inputs the digital signals to computer 30.

Radiation from source 16 is partly scattered by the elongated objects 10 in sensor region 12 such that radiation is forward scattered at a range of angles θ from each object. The sensor region encompasses a volume defined by the radius of the beam and the length along axis 24 between radiation source 16 and lens 18. The scattered radiation from large objects is strong and concentrated at small values of θ, while scattered radiation from smaller objects is weak and spreads out to larger values of θ. The scattered radiation impinges lens 18 at a location that is radially displaced from axis 24 by a distance based on angle θ. As more fully described in connection with FIG. 2, lens 18 projects the scattered radiation onto scatter detector 20 at the distance from central aperture 22 equal to θf.

In preferred embodiments, radiation receiving system 18 is a lens that refracts the radiation to scatter detector 20. In other embodiments, radiation receiving system 18 may consist of radiation handling components, such as mirrors, lenses and/or prisms, that direct radiation from a detection plane to a scatter detector where scattered radiation will impinge a location on the scatter detector based on angle θ.

In preferred embodiments, scatter detector 20 comprises an array of radiation detectors as shown in FIG. 3. In other embodiments, the scatter detector may comprise multiple detectors distributed over the detection surface. Alternatively, radiation pipes, such as optical fibers, may be used to collect scattered radiation from various locations in the detection plane and deliver the radiation to an array of detectors, such as a CCD array. The scatter detector may have a curved, planar or multi-planar detection surface.

In the preferred embodiment, the lens 18 is arranged to focus unscattered radiation through aperture 22. Thus, in the absence of objects 10 in the sensing region 12, beam 14 is focused by lens 18 through aperture 22 and onto radiation attenuation detector 26.

Radiation scattered by objects 10 in sensor region 12 reaches lens 18 at a range of non-zero scatter angles, denoted by θ, to the axis 24 of the beam. Consequently, instead of being focused on aperture 22, the scattered radiation is directed to a location on lens 18 radially distal to axis 24, based on scatter angle θ.

Figure 2:
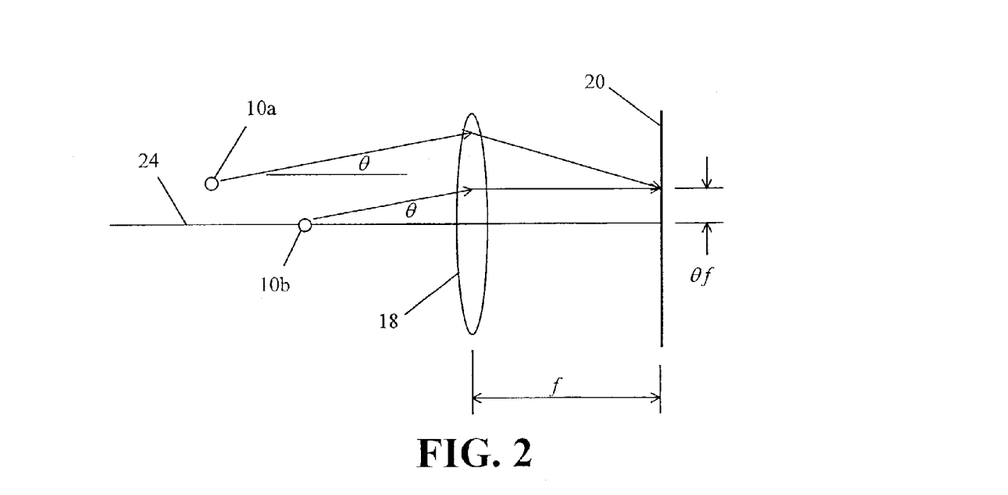
FIG. 2 is a schematic representation of a portion of the apparatus illustrated in FIG. 1, demonstrating insensitivity of the apparatus to the location of elongated objects in a sensor region.

FIG. 2 illustrates the arrangement of lens 18 and detector 20. Preferably, scatter detector 20 is positioned 1.0 focal length from lens 18. Objects 10a and 10b in sensor region 12 are at different locations along axis 24 and at different radial positions relative to axis 24. Although objects 10a and 10b scatter light at range of angles, a specific angle is considered for the sake of illustration.

Light scattered at a given angle θ from objects 10a and 10b impinges lens 18 at different radial locations due to the physical displacement of objects 10a and 10b from lens 18 and/or axis 24. Lens 18 is shaped so that scattered light from both objects 10a and 10b is refracted by lens 18 to the same radial distance on scatter detector 20, namely a position that is θf distance from aperture 22 on axis 24. More particularly, both the incident angle θ of scattered light radiation impinging lens 18 and the radial position of the impinging radiation on the lens define the refraction angle of the light from the lens to scatter detector 20. The lens is arranged so that light impinging the lens from different locations but at the same scatter angle θ is refracted to scatter detector 20 at a single radial distance from axis 24 and aperture 22. Since the focal length is the same for all objects in sensor region 12, variance in position of light impinging scatter detector 20 is based solely on the value of angle θ. The impinging light intensity increases due to plural objects projecting light onto the location at θf distance from aperture 22, so the set of intensity values of light at multiple radial positions is an indication of the distribution of the sizes of objects in the sensor region.

In preferred embodiments, scatter detector 20 is positioned 1.0 focal length from lens 18. This assures that the angular scattering patterns from randomly positioned objects 10 in sensor region 12 are overlapped without any bias due to the spacing between the scattering object and the lens.

As illustrated in FIG. 3, scatter detector 20 comprises an array of a plurality of concentric ring-shaped radiation detectors 32, 34 centered on aperture 22 and axis 24. The array is arranged in halves such that each detector 32 in the upper half and each detector 34 in the lower half is a circular segment encompassing a range of azimuthal angles φ. In preferred embodiments, φ is about 135°, although an azimuthal angle φ as small as about 30° is satisfactory in many cases.

Each detector 32, 34 has a unique radial width, and the detectors are arranged by width such that the detector widths increase with the radius of array 20. Thus, the detector 32 or 34 most distal from aperture 22 has the largest radial width, whereas the detector 32 or 34 closest to aperture 22 has the smallest radial width. Detectors 32 of the upper half of array 20 are radially offset, forming a non-detecting space 36 between radially adjacent detectors 32. The radial width of each space 36 is approximately equal to the width of a corresponding detector 34 in the lower half of the array at the same radial position. Similarly, detectors 34 of the lower half of array 20 are radially offset by non-detecting spaces 38 that are approximately equal to the width of a corresponding detector 32. In one preferred configuration, scatter detector 20 consists of an array of thirty-one rings with alternate rings located on the opposite halves of the array. In preferred embodiments, the widths of the individual ring detectors increase exponentially from axis 24.

In an alternative embodiment, the scatter detector may comprise a two-dimensional array of small detectors, like a CCD array. The output of these detectors may be grouped together selectively in the computer 30 to represent the array 20 described above. Similarly, the ring detectors in 20 may not physically have increasing widths, but their output may be combined in a fashion in the computer to represent increasing widths.

The apparatus illustrated in FIGS. 1–3 is particularly useful for process control during manufacture of elongated objects, such as glass or polymer fibers. A collimated radiation beam 14, such as a laser beam, is generated and expanded to about 1.0 cm diameter by laser source and beam expander 16. Beam 14 passes through sensor region 12 where newly-manufactured elongated objects 10 are passing in a direction generally at 90° to the axis 24 of the beam. Light scattered by the objects in the forward direction impinges scatter detector 20.

Lens 18 focuses the laser beam on aperture 22 through the scatter detector. The intensity of laser beam is detected by attenuation detector 26 to provide a signal to computer 30 representative of the intensity of the laser beam at aperture 22. The beam intensity at aperture 22 varies inversely with the density of the objects in sensor region 12. Thus, if the density of objects 10 is high, the laser beam is strongly attenuated at aperture 22 due to a high degree of scattering, thereby resulting in a low output from detector 26.

Scatter detector 20 detects intensity of light scattered by objects 10 at various angles θ. The inner rings detect radiation scattered at small angles and the outer rings detect radiation scattered at larger angles. The width of each ring defines a range of scatter angles θ that are detected by the ring. The range of scatter angles detected by each ring increases exponentially with the scatter angle θ due to the exponentially increasing width of the detector rings.

The scatter signals from scatter detector 20 and the attenuation signal from attenuation detector 26 are processed by computer 30 into a size distribution of the elongated objects. It is known that small-width objects scatter radiation over wider angles, but at smaller intensities, than large-width objects. This phenomenon is primarily due to diffraction characteristic of the objects. Consequently, the exponentially increasing radial width to the detector rings compensates for lower intensities of smaller objects diffracting light at large angles by encompassing a greater range of scatter angles.

Computer 30 contains a program that simulates digital masks correlating light intensities detected by ring detectors 32, 34 to the size (width) of elongated objects. Computer 30 compares the signals from scatter detector 20 to the digital masks to identify the distribution of fiber size in region 12. Computer 30 may provide output controls to the fabrication process to adjust parameters of the fabrication process, such as air temperature and pressure and furnace temperature for a meltblown process. Attenuation detector 26 provides a signal representing the amount of attenuation of the unscattered beam due to scattering and hence the density of fibers in region 12. The signal from attenuation detector 26 is also employed to estimate the extent of secondary scattering (light scattered by a fiber being secondarily scattered by another fiber).

In another embodiment the objects may be a collection of randomly oriented elongated objects such as a non-woven fiber web. In such a case, the fiber web is placed in sensor region to identify the distribution of fiber size in the web. This information is employed to catalog or classify the web based on fiber size.

One feature of the present invention is that the detectors 32, 34 of scatter detector 20 are increasingly wider at increased radial distances from center axis 24 and aperture 22. Since the forward-scattered light from smaller-width objects is of less intensity and is spread out to larger angles θ than that from larger-width objects, more light from smaller-width objects impinges the larger detectors 32, 34, thereby enhancing sensitivity of the apparatus to objects 10 having smaller widths. Consequently, the representation of smaller-width objects in region 12 is accurately identified using the scatter detector 20 according to the present invention.

Figure 4:
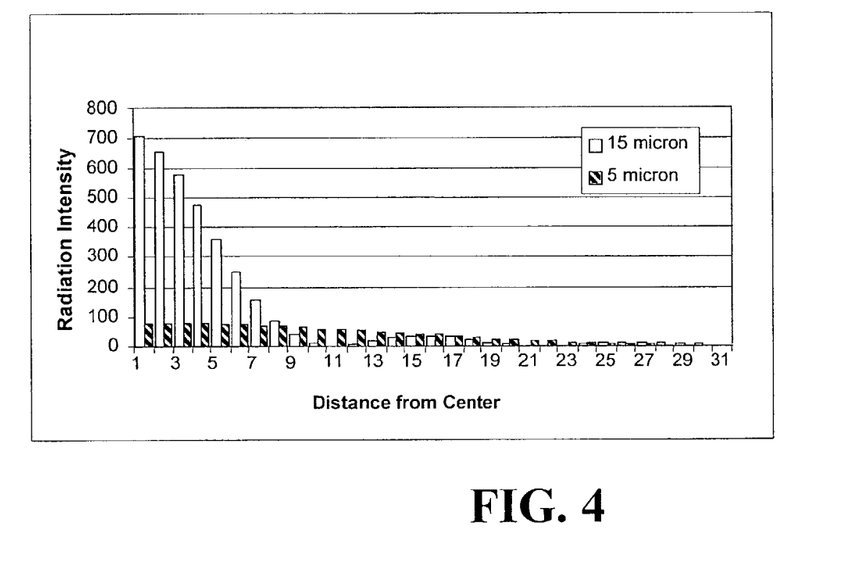
FIG. 4 is a graph illustrating radiation intensities at plural positions from an axis of a radiation beam due to radiation scattering from small- and large-width elongated objects.

This feature is illustrated in FIG. 4, which is a graph illustrating radial distributions of radiation intensities due to forward scattering of radiation from two elongated objects having widths of 15 and 5 microns, respectively. Prior constant-width detectors provided signals that closely matched the distribution of intensities shown in FIG. 4. This resulted in a large disparity between the signal strengths from the detector for the large and small objects. Thus, the signal strength due to scattering from 15 micron-wide objects is greater than, and tends to mask, signals due to scattering from 5 micron-wide objects. Hence, most prior detectors were unsuitable for identifying both large- and small-width objects.

Figure 5:
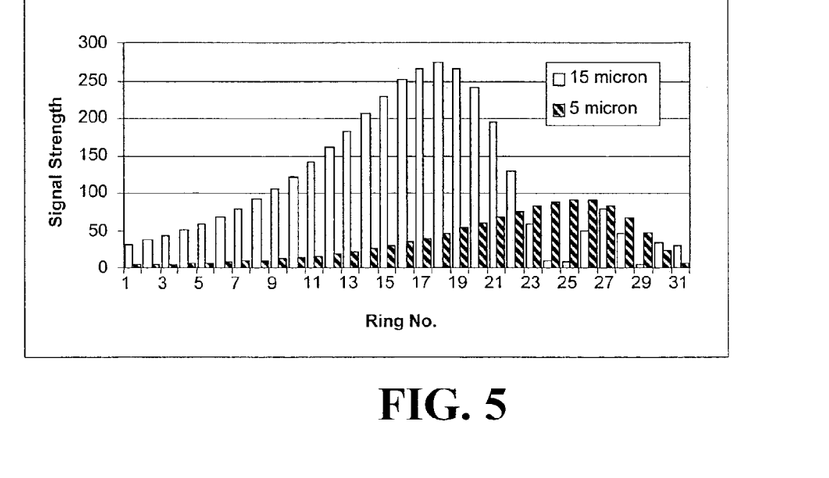
FIG. 5 is a graph illustrating detection signals derived by the scatter detector illustrated in FIG. 3 due to radiation scattering from small- and large-width elongated objects.

FIG. 5 is a graph of signal strengths from individual detectors of the array of detectors of scatter detector 20 according to one embodiment of the present invention. It will be appreciated from an inspection of FIG. 5 that while the signal strengths due to both 5 and 15 micron-wide objects is enhanced at greater distances from axis 24, the effect due to the smaller, 5 micron, objects is greater than on the larger, 15 micron, objects. As a result, the signal strengths due to the 5 micron wide objects is clearly discernable from the signal strengths due to 15 micron wide objects. Consequently, scatter detector 20 is capable of providing detection signals to computer 30 to identify both large- and small-width objects in sensor region 12.

The apparatus of the present invention is also insensitive to tilt of the elongated objects. The tilt of an elongated object may be defined in terms of two tilt angles, namely (1) rotation of the elongated object about axis 24 of the laser beam, and (2) forward or backward tilt ψ (FIG. 1) of the elongated object relative to axis 24 of the laser beam. Rotation of object 10 about axis 24 results in rotation of its scatter pattern along the azimuthal angle φ. Tilt ψ results in curving of the scatter pattern reaching lens 18.

In the apparatus of the present invention, the first tilt angle does not alter the detection signal because rotation of the object about axis 24 will rotate the scatter pattern about beam axis 24 so the radial displacement of the intensity pattern is unchanged. Regardless of the rotational position of object 10 to the beam axis 24, the arcuate shape of the ring detectors 32, 34 assures that the width of the object will be detected, even when the object is rotated about axis 24. Fibers that are measured during fabrication (on-line measurements) are typically oriented at tilt angles smaller than about ±30°, and can be accurately measured with the apparatus of the present invention. In the case of measurement of non-woven fiber webs (off-line measurements), all tilt angles are detected with equal probability, so loss of some tilt angles will not adversely affect measurement statistics. Therefore, as long as the object is within the range of the azimuth angles covered by the ring detectors, the present invention operates to measure widths of objects at various rotational positions about the beam axis.

Figure 6:
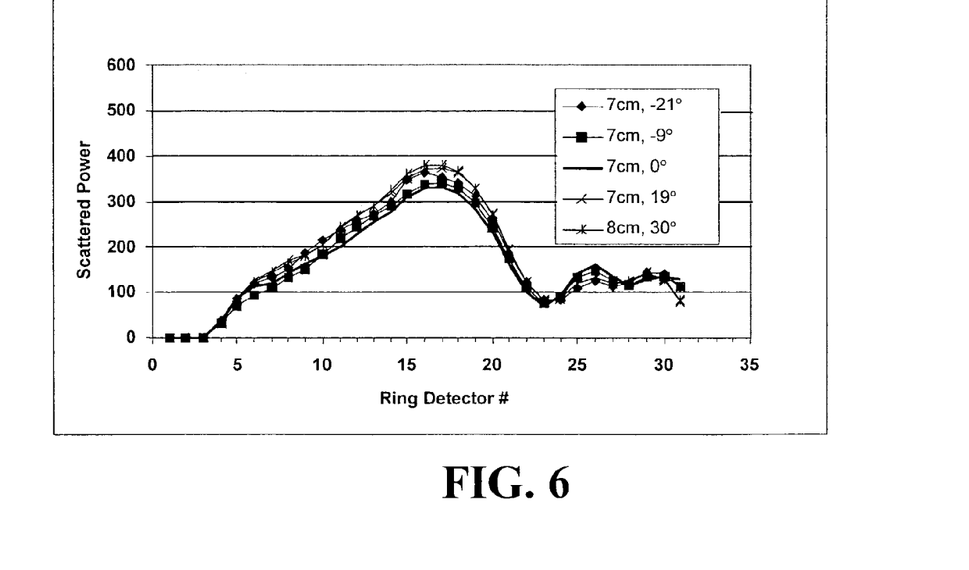
FIG. 6 is a graph illustrating measured scatter patterns of a plurality of fibers at various tilt angles.

The second tilt angle ψ will affect the detection signals of the scatter pattern. However, the experiments reveal that where forward or backward fiber tilt is within ±30° to normal orientation to the beam axis, the effect on the detection signals is negligible. FIG. 6 is a graph demonstrating a negligible change in signal intensity over the scatter detector due to backward-to-forward tilt angles ψ between −21° and +30° of elongated fibers located at distances of 7 to 8 cm from the lens. Hence, backward-to-forward fiber tilt as large as 30° does not adversely affect the measured scatter pattern to a significant degree.

The apparatus of the present invention makes it possible to collect the data that accurately represents the scattering of light by a plurality of elongated objects. A model, or digital mask, of the scattering of elongated objects of the type being measured is simulated in computer 30. From this model, computer 30 can identify the size distribution of the elongated objects 10 in sensor region 12. In preferred embodiments, the light scattering model is based on the Fraunhofer diffraction pattern, corrected for other effects discussed below.

Polymer and glass fibers (elongated objects) are frequently at least partially transparent, have an internal inhomogeneous structure, and often have a non-smooth surface. A Fraunhofer diffraction pattern is valid for opaque and smooth cylindrical objects. The Fraunhofer pattern may be affected by wide-angle scattering caused by the impurities and fine structure in the fibers, by small-angle scattering caused by the radial refractive index gradient in the fibers, and by secondary scattering in webs resulting from fibers scattering light previously scattered by other individual fibers. Further, the Fraunhofer diffraction theory suggests that the scattering intensity from an elongated object is modulated as a function of the scattering angle. In fibers, this modulation may be reduced due to any of several reasons, including the presence of non-smooth surfaces on the fibers, transparency of the fiber material and internal inhomogeneous structure of the fibers. In preferred embodiments, the conventional Fraunhofer model is adjusted empirically to derive an accurate conversion model of the forward scattering pattern for expected fiber types and sizes.

Figure 7:
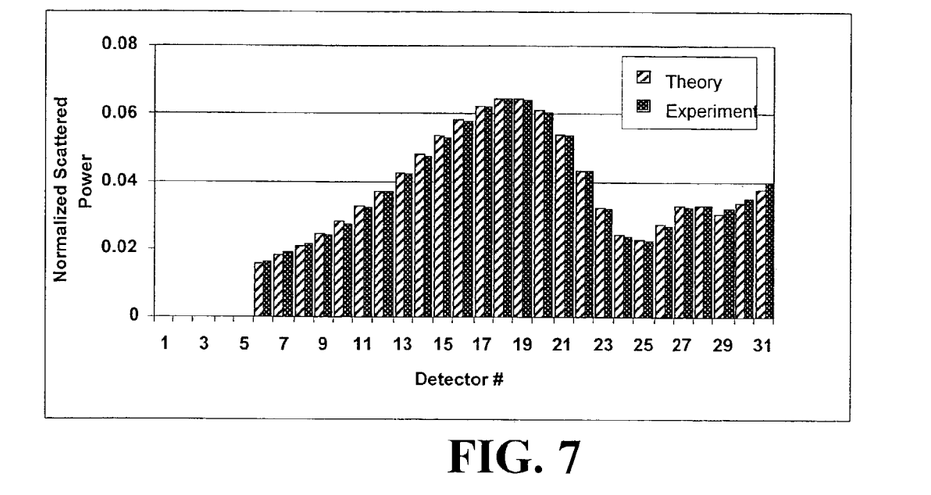
FIGS. 7 and 8 illustrate an example of the use of the apparatus and process of the present invention.
Figure 8:
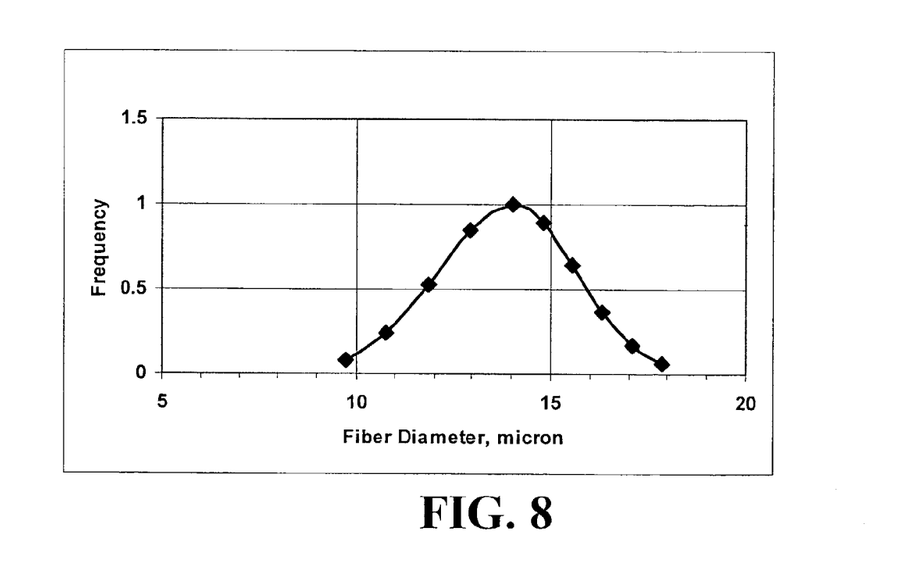

FIGS. 7 and 8 illustrate application of the present invention to measurement of a distribution of sizes of randomly-sized, randomly-oriented elongated objects. FIG. 7 illustrates signal intensities from detectors 32, 34 of scatter detector 20. A first set of intensities (shown in hatch) represents a set of theoretical intensities calculated for a plurality of randomly-oriented fibers of known size distribution. The second set of intensities (shown in black) represents a measured set of intensities for the same set of randomly-oriented fibers. Noteworthy, the computer is able to find a size distribution (shown in FIG. 8) whose theoretical scattering pattern closely matches the measured (experiment) intensities at each ring 32, 34.

Using empirically-derived digital masks, and compensating for attenuation and secondary scattering using a signal from attenuation detector 26, the distribution of object sizes can be identified, as shown in FIG. 8. FIG. 8 is a normalized chart of fiber size distribution based on the experimental curve shown in FIG. 7. Hence, the signal distribution derived from scatter detector 20 and illustrated in FIG. 7 is processed by computer 30, using empirically-derived digital masks, to identify the distribution of fiber sizes in the sensor region. The curve of FIG. 8 shows that the plural fibers resulting in the curve of FIG. 7 has a mean size (width or diameter) of about 14 microns with the size distribution between about 10 and 18 microns.

The present invention employs a lens/detector arrangement that refracts light forward scattered from an object at an angle θ to impinge scatter detector 20 at a radial position θf from the axis, regardless of the position of the object in the sensor region. Consequently, the radiation intensities at various radial positions on scatter detector 20 represent the scattered intensities as a function of the scatter angles θ, regardless of the position and orientation of the objects in the sensor region. Consequently, scattering patterns of randomly located scattering objects can be measured.

It is not necessary to position objects 10 to any restricted location between source 16 and lens 18. Consequently, sensor region 12 can be quite large. This feature renders the invention particularly useful for measuring fiber size distribution during manufacture of plural fibers, such as across parallel paths of fibers exiting a line of orfii in a meltblown process. Consequently, axis 24 may be positioned through the parallel fiber paths to provide an accurate measure of fiber size distribution even though some fibers are more distal from lens 18 and detector 20 than other fibers.

While sensor region 12 may be large along axis 24, it is important that the radiation receiving system, such as lens 18, have a radius large enough to receive representative light scattered from the objects distal the lens. Larger radius radiation receiving systems are required for larger scatter angles θ and for larger distances of the object to the lens. The maximum radius of the radiation receiving system is a function of the radiation wavelength, the scatter angle, and the distance of the elongated object from the lens.

For a given radiation wavelength, small objects scatter diffracted radiation at larger scatter angles than larger objects. Hence, larger ranges of scatter angles need to be covered in order to measure smaller objects. As an example, fibers with diameters of about 2 microns would be satisfactorily characterized if scatter radiation having a wavelength of 0.67 microns was sampled over a range to about 7.5°. At the same radiation wavelength, fibers with diameters of about 1 micron would require scatter radiation over a range to about 15° for a satisfactory size measurement. For a given range of scatter angles, the object size capable of being measured will vary with radiation wavelength. For example, fibers with diameters of about 1.4 microns would be characterized effectively using scatter radiation over a range to about 7.5° where the radiation wavelength is 0.4 microns.

Large objects scatter radiation at smaller scatter angles than smaller objects. Consequently, an upper size limit for measuring objects is, in part, limited by the size of aperture 22. The size limit can be increased by increasing the focal length f of lens 18. For example, for an aperture 22 having a diameter of about 100 to 300 microns, fibers with diameters as large as several hundreds of microns can be measured by using a focal length of about 100 millimeters.

The signal from attenuation detector 26 may be used to establish correction for the output of the scattering detector 20 to compensate for noise introduced into the scatter pattern due to secondary scattering.

The present invention thus provides a process and apparatus for on-line and off-line measurements of plurality of elongated objects, such as fibers, that may have random orientation, random location and may represent a range of sizes.

Although the present invention has been described with reference to preferred embodiments, workers skilled in the art will recognize that changes may be made in form and detail without departing from the spirit and scope of the invention.

What is claimed is:

1. Apparatus for detecting a width of an elongated object comprising, in combination:
   a radiation source for emitting a beam of radiation relative to an axis;
   a sensor region for receiving elongated objects and arranged relative to the beam so that the objects scatter radiation in a forward direction;
   a scatter detector having a plurality of radiation detectors responsive to impinging radiation intensity to provide a signal representative of impinging radiation intensity, wherein each radiation detector has a respective radial width and the radiation detectors are arranged relative to the axis by width; and a radiation receiving system positioned relative to the sensor region to transform radiation scattered by the objects to locations on the scatter detector based on the scatter angles of the scattered radiation.

2. Apparatus of claim 1, wherein the radiation detectors are arcuately arranged about the axis over an azimuthal angle of at least 30°.

3. Apparatus of claim 1, wherein the sensor region encompasses a volume defined by a radius of the beam and a length along the axis between the radiation source and the radiation receiving system, the apparatus being arranged to measure a distribution of widths of objects within the sensor region.

4. Apparatus of claim 1, wherein the radiation detectors are arranged about the axis of the radiation beam, so that each radiation detector detects radiation impinging the array of detectors at mutually respective radial distances from the axis.

5. Apparatus of claim 4, wherein the radiation detectors are arranged so that the radiation detector having the largest width is most distal from the axis.

6. Apparatus of claim 5, wherein the respective widths of the radiation detectors increase exponentially from the axis.

7. Apparatus of claim 1, further including an attenuation detector responsive to radiation impinging the scatter detector at the axis to provide a signal representative of beam intensity.

8. Apparatus of claim 7, wherein the attenuation detector comprises:
an axial aperture through the detector array, and
a second radiation detector responsive to radiation passing through the aperture to provide the signal representative of beam intensity.

9. Apparatus of claim 1, further including:
a processor responsive to the signals from the radiation detectors to generate an identification of a distribution of sizes of objects in the sensor region.

10. Apparatus of claim 9, wherein the processor includes a model that correlates sizes of elongated objects to distributions of scatter radiation intensities over the scatter detector, and the processor is programmed to compare signals from the scatter detector to the model to identify a distribution of widths of the elongated objects.

11. Apparatus of claim 10, wherein the model is based on a Fraunhofer pattern.

12. Apparatus of claim 10, wherein the model is empirically derived from samples of objects expected in the sensor region to compensate for factors selected from the group consisting of secondary scattering, wide-angle scattering, small-angle scattering and modulation changes.

13. A process of measuring a distribution of sizes of a plurality of elongated objects in a sensor region, comprising steps of:
a) scattering radiation from objects in the sensor region at a range of forward scatter angles;
b) transforming the scattered radiation to locations on a scatter detector based on the scatter angles, wherein the scatter detector has a plurality of radiation detectors arranged by width relative to an axis; and
c) sensing an intensity of radiation at each position on the scatter detector.

14. The process of claim 13, wherein step (a) includes steps of:
a1) directing a radiation beam into the sensor region along the axis, and
a2) scattering beam radiation from the objects,
and wherein the scattered radiation is refracted to respective locations without regard to axial location of the objects in the sensor region.

15. The process of claim 13, wherein step (c) includes steps of:
c1) defining a model that correlates sizes of elongated objects to distributions of scatter radiation intensities over the scatter detector, and
c2) comparing the sensed scatter radiation intensities to the model to identify the distribution of widths of the elongated objects.

16. The process of claim 15, wherein the model is based on a Fraunhofer pattern.

17. The process of claim 15, wherein the model is empirically derived from samples of objects expected in the sensor region to compensate for factors selected from the group consisting of secondary scattering, wide-angle scattering, small-angle scattering and modulation changes.

18. The process of claim 13, wherein step (a) includes steps of:
a1) directing a radiation beam into the sensor region along an axis, and
a2) scattering beam radiation from the objects,
the process further including:
d) sensing an intensity of radiation impinging an axial point on the scatter detector to identify an attenuation of the radiation beam in the sensing region.

19. The process of claim 18, wherein radiation scattered at respective scatter angles are transformed to respective locations on the scatter detector without regard to axial location of the objects in the sensor region.

20. The process of claim 13, wherein step (c) includes deriving a plurality of detector signals based on radiation intensities scattered at respective ranges of scatter angles.

21. The process of claim 20, wherein the radiation detectors have progressively greater widths radially distal from the axis.

22. The process of claim 21, wherein the radiation detectors are arranged over an azimuthal angle of at least 30°.

23. An apparatus comprising:
a radiation source for emitting radiation relative to an axis;
a sensor region for receiving an object so that the object scatters the radiation; and
a scatter detector having a plurality of radiation detectors responsive to impinging radiation intensity scattered by the object, wherein the radiation detectors are arranged relative to the axis by width.

24. The apparatus of claim 23 wherein each radiation detector has a respective radial width, and the radiation detectors are arranged relative to the axis by width so that the radiation detector having the largest width is most distal from the axis.

* * * * *